United States Patent [19]

Genba et al.

[11] Patent Number: 4,809,493

[45] Date of Patent: Mar. 7, 1989

[54] WATER-ABSORBING SHRINKABLE YARN

[75] Inventors: Tsuneo Genba; Junichi Yoshinaka; Shingo Nakanishi, all of Okayama, Japan

[73] Assignee: Kuraray Company Limited, Kurashiki, Japan

[21] Appl. No.: 921,117

[22] Filed: Oct. 21, 1986

[30] Foreign Application Priority Data

Nov. 1, 1985 [JP] Japan .................................. 60-246914
Dec. 27, 1985 [JP] Japan .................................. 60-297942
Jul. 4, 1986 [JP] Japan .................................. 61-158302

[51] Int. Cl.$^4$ .......................... D02G 3/04; D02G 3/26; D02G 3/44; A41B 13/02
[52] U.S. Cl. ........................................ 57/238; 57/252; 57/255; 604/376
[58] Field of Search ............... 57/351, 254, 255, 238; 112/412; 28/281, 156; 604/367, 375-377

[56] References Cited

U.S. PATENT DOCUMENTS

| | | | |
|---|---|---|---|
| 2,701,406 | 2/1955 | Bloch ................................ | 57/254 |
| 3,146,574 | 9/1964 | Earnshaw .......................... | 57/254 |
| 3,388,547 | 6/1968 | Koga et al. ....................... | 57/351 |
| 3,424,833 | 1/1969 | Mazzolini et al. ............... | 57/351 X |
| 3,490,223 | 1/1970 | Mazzolini et al. ............... | 57/254 |
| 3,587,220 | 6/1971 | Eggleston ......................... | 57/351 X |
| 4,357,938 | 11/1982 | Ito et al. .......................... | 604/376 |
| 4,406,660 | 9/1983 | Beiner et al. .................... | 604/376 |

Primary Examiner—John Petrakes
Attorney, Agent, or Firm—Oblon, Fisher, Spivak, McClelland & Maier

[57] ABSTRACT

Rapidly shrinking fibers hardly soluble in water and capable of shrinking in water at 20° C. by not less than 30% in not longer than 10 seconds are obtained, for example, by spinning, drawing and heat-treating a carboxy-modified polyvinyl alcohol under specific conditions. Yarns made from a fiber of this kind in conjunction with a fiber slowing shrinking in water as well as nonwoven fabrics made by incorporating yarns containing said rapidly shrinking fibers in nonwoven fabric shrinkable upon absorption of water are suited as means of tightly fitting edge portions of disposable diapers to the thigh.

4 Claims, 3 Drawing Sheets

WATER-ABSORBING SHRINKABLE YARN

BACKGROUND OF THE INVENTION

1. Field of the Invention

This invention relates to a fiber capable of rapidly shrinking when coming into contact with water at ordinary temperature and capable of maintaining the fiber form and exhibiting performance characteristics such as rubber elasticity, to a yarn made by using said fiber, capable of rapidly shrinking in the lengthwise direction upon absorption of water at a high rate of appearance of shrinkage stress and capable of exhibiting high strength and rubber elasticity for a prolonged period of time even after water absorption and shrinkage, and to a water-absorbing shrinkable material made by incorporating into a nonwoven fabric shrinkable upon absorption of water a yarn (yarn, twist yarn, cord, or the like) made from said fiber and shrinkable more rapidly and to a greater extent as compared with said nonwoven fabric.

2. Description of the Prior Art

Fibrous materials which, when immersed in water, can absorb water under swelling or dissolution have been known so far. For instance, polyvinyl alcohol (hereinafter abbreviated as "PVA")-based water-soluble fibers derived from hydrophilic group-containing resins, and highly water-absorbent fibers modified by incorporation of hydrophilic groups while they are in fibrous form are known widely. However, these fibers are used either as fibrous adhesive for other materials or for the purpose of temporarily fixing other raw materials to maintain their processability. In the latter case, said fibers are finally removed by dissolution. In some instances, such fibers are used for the mere purpose of water absorption. Thermally shrikable fibers made of hydrophobic resins are also known but they are shrinkable only in a relatively high temperature range exceeding 60° C.; they solidify upon cooling and therefore do not show rubber elasticity.

The present inventors have previously proposed a fiber made of PVA and capable of shrinking in water to a great extent in Japanese Laid-Open Patent Publication No. 60-2709. However, this fiber required 30 seconds for 30% shrinkage even in water at a temperature of 30° C. and shows a very slow rate of shrinkage when ordinary temperature water (in the neighborhood of 20° C.) is used, although it is excellent in that it is hardly soluble.

A primary object of the invention is to provide a fiber which can respond to water very sensitively when in comes into contact with water at 20° C., for instance, and can shrink greatly without substantial dissolution.

Yarns capable of shrinking upon absorption of water and knitted or woven fabrics made of such yarns are useful in a variety of applications. For example, when such shrinkable yarns are used in lengthwise edge portions of disposable diapers, the yarns absorb water excreted by the users of the disposable diapers (mainly water contained in urine, diarrheal stool, etc.) and shrink, so that urine, stool and the like can be prevented from escaping from such disposable diapers (e.g. U.S. Pat. No. 4,357,938 and West German Patent No. 3,130,241). When said shrinkable yarns are used as various fastening strings and allowed to absorb water in the fastened portions, they can prevent the fastened portions from loosening thanks to the appearance of shrinkage stress upon absorption of water. When cloths made of such shrinkable yarns are used as water roll coverings in offset printers, cylinders somewhat greater in diameter than the core roll are made of said cloths in advance. When they are mounted on the core roller and immersed in water, the cylindrical coverings can come into close contact with the core roll, so that the mounting procedure can be much simplified. Furthermore, coarse-textured cylinders or cords made of said shrinkable yarns can be mounted on plant roots on the occasion of plant transplantation in a simple manner for the same reason as in the case of the above-mentioned water roll coverings for offset printers. In addition, such yarns are useful in manufacturing nets or strings for ham and the like. Cloths of said kind as made for civil engineering purposes, when once subjected to water absorption treatment, for instance, acquire very high shock resistance with high-degree elongation and can be used as excellent sheets for preventing bank-protecting basements from being washed away or scooped out by waves, for instance. The yarns are also useful as humidity sensors.

As is suggested by the applications mentioned above, it is essential that water-absorbing shrinkable yarns should meet four requirements, namely high rate of shrinkage and high of appearance of shrinkage stress upon absorption of water, retention of high strength for a prolonged period of time even after absorption of water, and appropriate degree of rubber-like elasticity. These requirements should be met at the same time.

Various yarns capable of shrinking upon absorption of water have been so far proposed. However, the prior art water-absorbing shrinkable yarns cannot meet at least one of the above four requirements, hence are never satisfactory. For instance, those yarns that show increased rate of shrinkage and increased rate of appearance of shrinkage stress upon absorption of water contain a hydrophilic polymer as a fiber-constituting polymer and have a structure such that water can easily invade the fiber inside. Furthermore, such yarns have an increased degree of orientation of fiber-constituting molecules so that fibers swelled with invading water can contribute to shrinkage in the direction of fiber axis. In this manner, such fibers have a structure such that they can swell freely upon absorption of water. Therefore, the fiber inside structure can be readily disintegrated upon absorption of water and, as a result, the strength and shrinkage stress after absorption of water and shrinkage decrease rapidly. A conceivable method of increasing the strength and shrinkage stress after water absorption and shrinkage would comprise twisting said yarns to a high number of twist so that the internal structure can hardly be disintegrated. Since, however, such yarns have a compact structure, water can hardly invade the yarn inside and at the same time the free space in which fibers can swell is limited even when yarn-constituting fibers absorb water. For these and other reasons, the rate of shrinkage and rate of appearance of shrinkage stress upon absorption of water are markedly reduced. Thus, the hitherto known water-absorbing shrinkable yarns are deficient in at least one of the performance characteristics, rate of shrinkage upon absorption of water, rate of appearance of shrinkage stress, strength after water absorption and shrinkage and rubber-like elasticity after water absorption and shrinkage, and accordingly encounter problems in their use in various fields such as mentioned above.

Accordingly, it is a second object of the invention to provide a water-absorbing shrinkable yarn which can meet all the above four requirements, namely a yarn which is high in rate of shrinkage upon absorption of water, high in rate of appearance of shrinkage stress and high in strength after water absorption and shrinkage, and has rubber-like elasticity after water absorption and shrinkage.

The prior art relative to the above-mentioned disposable diapers is described in the following in further detail. While various disposable diapers have been proposed so far, the edge portions of disposable diapers should have a function such that said edge portions should be in close contact with the thigh in order to prevent leakage of urine and so forth. The following three structures are known as the means therefor.

(a) The use of an elastomer (in the form of a tape or yarn), such as polyurethane or rubber, in edge portions of disposable diapers. Said edge portions are kept in close contact with the thigh of users by the elasticity of said elastomer.

(b) The use of yarns shrinking upon absorption of water in edge portions of disposable diapers. Said water-absorbing shrinkable yarns absorb urinary water and so on and said edge portions are brought into contact with the thigh of users through the shrinkage taking place on that occasion.

(c) Combined use of the above methods (a) and (b).

Among these three methods, method (b) is preferred to method (a) because packed products before use are less bulky and more handy to carry and furthermore less causative of stuffiness. Therefore, they have been commercialized recently. An example of the transverse section of such a product is shown in FIG. 10, where 15 is a back sheet made of a polyethylene film about 25 μm in thickness, 16 is a water absorbent for absorbing water such as urine, 17 is a front sheet, 18 is a water-absorbing shrinkable yarn for bringing the edge portion of the disposable diaper into close contact with the thigh, and portions B are sealing portions for securing water-absorbing shrinkable yarns at predetermined sites (the back sheet and front sheet are adhered together in said portions). Disposable diapers which use this method (b) indeed have outstanding features such as mentioned above but are still disadvantageous in that when a larger quantity of water than that absorbable by the water-absorbing shrinkable yarn reaches an edge portion, the shrinking of the water-absorbing shrinkable yarn is too late to prevent water from escaping out of the edge portion. The prior art avoids this phenomenon by positively introducing part of water absorbed in the water absorbent to the water-absorbing shrinkable yarn by utilizing an auxiliary means such as an absorbent paper as early as possible so that the shrinkage of the water-absorbing shrinkable yarn can be caused prior to spontaneous arrival of water absorbed by the water absorbent at the edge portion (the absorbent paper shown by 19 in FIG. 10 functions in this manner), as disclosed in Japanese Laid-Open Patent Publication No. 57-35002 (i.e. the above-cited U.S. Pat. No. 4,357,938 or the above-cited West German Patent No. 3,130,241) or Japanese Laid-Open Patent Publication No. 57-56502, for instance. However, this technique, too,,has failed to solve the leakage problem since the shrinkage of the water-absorbing shrinkable yarn cannot take place in time when diapers are used in an extraordinary condition (e.g. when users urinate while lying on their side or when users discharge diarrheal stool violently).

When, in using a water-absorbing shrinkable yarn in edge portions of disposable diapers, the water absorbent and the water-absorbing shrinkable yarn are superposed on each other, the edge portions fail to shrink because the water absorbent itself is bulky and does not shrink. Therefore, it is essential in the prior art that the water-absorbing shrinkable yarn should be located almost alone in the edge portions of disposable diapers without overlapping with the water absorbent (cf. the above cited Japanese Laid-Open Patent Publication No. 57-35002 and No. 57-56502). The water-absorbing shrinkable yarns to be used in the edge portions of disposable diapers generally have a diameter of about 0.5–0.7 mm and therefore its single use may bring about an occurrence of impressions caused by constriction on the thigh when said portions are kept in close contact with said thigh. Although such impressions are harmless to users from the medical viewpoint, they may serve as a factor making mothers anxious about them especially when the users are their babies. This is also a great problem which method (b) faces.

Method (c) has the same problem as mentioned above since it is a mere combination of method (a) and method (b).

Accordingly, it is a third object of the invention to provide a water-absorbing shrinkable material usable in manufacturing disposable diapers having ideal performance characteristics, namely such that when used as a shrinkable material in edge portions of disposable diapers, said water-absorbing shrinkable material prevents leakage from said disposable diapers without causing impressions of constriction on the thigh with little stuffiness in the crotch and also renders compact the folded form of the disposable diapers before use.

SUMMARY OF THE INVENTION

The above first object of the invention can be achieved by providing a fiber which hardly soluble in water but is rapidly shrinkable in the presence of water with the following characteristics as measured in water at 20° C.: a maximum shrinkage of not less than 30%, a time required for reaching 30% shrinkage of not longer than 10 seconds, a shrinkage stress in the original length state of not less than 150 mg/dr, a time required for the shrinkage stress of 150 mg/dr of not longer than 10 seconds, a shrinkage stress at the 30% shrinkage relative to the original length of not less than 30 mg/dr and a weight loss due to dissolution in the dispersed state in water at 20° C. of not more than 45%. (Hereinafter, the invention concerned with this rapidly shrinking fiber is referred to as the first invention.)

The above second object of the invention can be accomplished by providing a water-absorbing shrinkable yarn made by mix twisting or mix spinning said rapidly shrinking fiber and a fiber shrinking more slowly upon absorption of water than said fiber. (Hereinafter, the invention concerned with this water-absorbing shrinkable yarn is referred to as the second invention.)

Furthermore, the above third object of the invention can be accomplished by providing a water-absorbing shrinkable material composed of a nonwoven fabric shrinkable upon absorption of water and a yarn shrinkable at a higher rate and to a higher extent upon absorption of water than said nonwoven fabric with said rapidly shrinking fiber being contained in said water-absorbing shrinkable yarn. (Hereinafter, the invention concerned with this water-absorbing shrinkable material is referred to as the third invention.)

BRIEF DESCRIPTION OF THE DRAWINGS

In the accompanying drawings.

DETAILED DESCRIPTION OF THE PREFERRED EMBODIMENT

Figure 1:
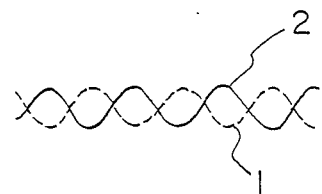
FIG. 1 is a schematic representation of a yarn made by twisting together a rapidly shrinking fiber (1) and a non-shrinking fiber (2)

The first invention mentioned above is described in further detail in the following.

In an increasing number of fields, fibrous materials capable of sensing water and shrinking rapidly when they come into contact with water at ordinary temperatures are required. For expressing the rate of shrinking in evaluating such materials with respect to practical utility, the time required for attaining the shrinkage percent of 30% is used herein. For the rapidly shrinking fiber as disclosed herein, said time should be not longer than 10 seconds, preferably not longer than 7 seconds. Since it is a prerequisite that the fiber should retain rubber elasticity after shrinkage, the shrinkage stress at the stage where the shrinkage is 30% should desirably be as high as possible from the fiber volume and economy viewpoints. In accordance with the present invention, the following performance characteristics as determined in water at 20° C. could be obtained: maximum shrinkage of not less than 30%, time required for reaching 30% shrinkage of not longer than 10 seconds, shrinkage stress in the original length state of not less than 150 mg/dr, time required for the shrinkage stress to reach 150 mg/dr of not longer than 10 seconds, and shrinkage stress in the state of 30% shrinkage relative to the original length of not less than 30 mg/dr. However, even when these shrinkage rate and shrinkage stress are secured, excessive swelling must be prevented so that the state of shrinkage, in particular shrinkage stress, can be maintained for a prolonged period of time. Therefore, the weight loss due to dissolution as determined by dispersing fiber pieces about 10 mm in length in the free state in water at 20° C. in a bath ratio of not less than 200, allowing the suspension to stand and measuring the weight loss after 60 minutes of standing is required to be not greater than 45%, preferably not more than 25%.

It is widely known that the use as raw materials of PVA derivatives obtained by introducing a variety of modifying groups is preferable for improving the affinity for water of fibers which have sufficient strength for their practical use. PVA or modified PVA is a preferred raw material for use in the practice of the first invention. In particular from the viewpoints of rapid shrinking in water and scarce solubility suitable are modified PVA species, such as carboxyl group-modified PVAs, cationic group-containing PVAs and sulfo group-containing PVAs. Among them, carboxy-modified PVAs, such as itaconic acid-modified PVA and maleic acid-modified PVA, in particular itaconic acid-modified PVA, are preferred. In the case of carboxy-modified PVAs, preferred from the fiber production and performance viewpoints are those which have a carboxy modification degree of 0.5–10 mole percent, an average polymerization degree of 500–3,000 and a saponification degree of 79–99.9 mole percent, more preferably a modification degree of 1.5–5 mole percent, an average polymerization degree of 1,000–2,000 and a saponification degree of 86–99 mole percent. The term "carboxy modification degree (content in mole percent)" as used herein for the modified polyvinyl alcohol means the mole percent of the carboxyl group-containing monomer based on the total amount of vinyl acetate and the carboxyl group-containing monomer as used in synthesizing the modified polyvinyl alcohol.

The carboxy-modified PVA can be spun into a fiber either by the dry method or by the wet method. However, it is economical to employ the dry spinning mode since said PVA is highly hydrophilic. Thus, an aqueous solution of the carboxy-modified PVA having a concentration of 35–60%, preferably 50–55% is used as the spinning solution. For spinning, a particular spinning process quite different from the ordinary dry spinning method for vinylon is used and the filaments spun out are subjected to drawing and heat reatment. The drawing ratio should be at least 4 times so that internal strain may remain within the fiber to secure a required rate of shrinkage.

In Japanese Patent Publication No. 53-10174, there is proposed a similar process. However, the object of this proposal is to produce a fiber which is soluble in water at low temperatures and the proposal is characterized by low-temperature drawing and heat treatment at 100°–180° C. Thus it is quite different from the present invention. Fibers obtained by the method described in the above-cited patent specification, when brought into contact with water at ordinary temperatures, are almost wholly or quite wholly dissolved in water within a short period of time, that is to say they are entirely deficient in water resistance. On the contrary, the rapidly shrinking fiber according to the invention can remain for the most part in the fiber form even after long-period immersion in water; it has thus the so-called water resistance.

Partial hydroxyl group blocking with an aldehyde, for instance, is a method in use for providing PVA fibers with water resistance. For such strong hydrophilic property as required in the practice of the invention to be maintained, the degree of acetalization should be extremely low and, for rendering such fibers scarcely soluble or insoluble, the use of a dialdehyde which is to bring about intermolecular crosslinking is effective. However, in the case of highly hydrophilic carboxymodified PVA fibers, it is impossible or economically not preferable to subject an aldehyde to reaction in an aqueous system.

In the case of ordinary PVA fibers, it is also possible to improve them in water resistance by raising the temperature in drawing and heat treatment to thereby increase the crystallinity of fiber-constituting molecules. However, it is well known among those skilled in the art that the phenomenon of crystallization brought about by such technique results in decrease in shrinking behavior at low temperatures which is more remarkable as compared with the dissolution temperature-raising effect.

Surprisingly, however, it has been found that even when the drawing and heat treatment temperature is 190° C. or above, the scarce solubility in water at 20° C. of modified PVA fibers made by using a carboxy-modified PVA can be improved markedly almost without any change in rapid shrinking property in water at 20° C.

On the other hand, as is indicated in Japanese Patent Publication No. 53-10174, the maximum drawing ratio employable rapidly decreases to 3.5 or less and the scarce solubility in water and the shrinkage percentage that are required can hardly be secured when the drawing and heat treatment temperature exceeds 190° C.

As a result of their intensive study, the present inventors have invented fibers having rapid shrinking property as well as scarce solubility in water by employing a particular spinning mode to thereby make it possible to achieve a maximum drawing ratio of 4 or more. Thus, those drawing and heat treatment conditions required for providing scarce solubility in water and rapid shrinking property, namely a drawing temperature of 190°–230° C. and a drawing ratio of 4–7, have become reasonably employable by forcing a spinning solution, which is an aqueous solution of a carboxy-modified polyvinyl alcohol having a concentration of 35–60%, through a nozzle at a spinning solution temperature of 95°–160° C., applying immediately thereafter a particular spinning chimney comprising a cooling zone having a length of 0.1–1.0 m and adjusted to a temperature of 20°–70° C., preferably 20°–50° C., and a pre-drying zone having a length of 1–8 m and adjusted to a temperature of 80°–170° C., preferably 90°–140° C., to thereby form fibers, and then drying the fibers to almost bone dry at a temperature of 110°–145° C. When the drawing temperature is below 190° C., it is impossible to provide satisfactorily scarce solubility in water whereas, at temperatures above 220° C., fibers being to discolor and the discoloration may become an obstacle in cases where the appearance is an important quality feature. Therefore, the drawing and heat treatment should preferably be carried out within the temperature range of 200°–215° C.

The drawing ratio preferably lies within the range of 4–7 from the fiber performance and productivity viewpoints. It is desirable to use a relatively high drawing ratio at relatively high treatment temperatures.

Conceivable fields of use of the rapidly shrinking fiber according to the first invention include, but are not limited to, side edge fastening strings in disposable diapers to be mentioned later herein, moisture-detecting sensors, tying yarns for fishing implements, fastening strings for use in plant grafting, and strings to be wound round plant roots.

The second invention is now described in more detail.

While high rates of shrinkage upon absorption o water and high rates of shrinkage stress appearance are characteristic of fibers capable of rapidly shrinking upon absorption of water, typically the fibers according to the first invention mentioned above, such fibers are still have a disadvantage, that is to say, the strength and shrinkage stress after water absorption and shrinkage decrease in a short period of time. On the other hand, fibers shrinking slowly upon absorption of water show high strength and high shrinkage stress after water absorption and shrinkage but are still disadvantageous in that they shrink too slowly upon absorption of water with too slow shrinkage stress appearance. The second invention is based on the finding that the respective advantages of the two kinds of fibers can be enhanced and the respective drawbacks can be removed when said two kinds of fibers each having its advantages and disadvantages such as mentioned above are combined and united together. In accordance with the second invention, the two kinds of fibers are combined to give yarns by means of mix twisting or mix spinning. This means of combining is preferred in extending the advantages and removing the drawbacks the fibers respectively have.

The water-absorbing shrinkable yarn according to the second invention is further described in the following, taking, as an example, the case of its use in the lengthwise edge portions of disposable diapers. In such case, it is required in particular that the rate of shrinkage as well as the rate of appearance of shrinkage stress should be high. If the rate of shrinkage of the water-absorbing shrinkable yarn upon absorption of water or the rate of appearance of shrinkage stress is slow, and if the excretion of the body fluid by the users of disposable diapers is abrupt and violent (e.g. when the users discharge violent diarrheal stool or when they urinate while lying on their side), the excrement would leak out of the disposable diapers over the edge portions thereof before the water-absorbing shrinkable yarns mounted on the disposable diapers can function enough (i.e. before the side edges of disposable diapers can come into sufficiently close contact with the thigh of users). Furthermore, since users of disposable diapers generally move frequently, the water-absorbing shrinkable yarns experience elongation and shrinkage repeatedly, and the side edge portions of disposable diapers must be always in close contact with the thigh. Even when disposable diapers are used in an abnormal condition (e.g. when they are not worn or maintained in a normal condition or when users move violently), the water-absorbing shrinkable yarns must not break. For meeting all these requirements, it is required that the yarns after water absorption and shrinkage should retain an adequate degree of rubber elasticity and a sufficient degree of strength. The water-absorbing shrinkable yarns used in the side edge portions of disposable diapers shrink upon absorption of water contained in the excrement from users. On such occasion, the body fluid discharged does not always reach the water-absorbing shrinkable yarns immediately. It is to be anticipated that a new portion of excrement might be discharged after absorption of an excrement by the absorbent in disposable diapers and fall of the temperature thereof and that, thereafter, the old and new portions might arrive in admixture at the water-absorbing shrinkable yarns.

The shrinkage percentage, rate of shrinkage, shrinkage stress, rate of shrinkage stress appearance, degree of swelling, stress relaxation after swelling and so forth of an organic macromolecular material naturally depend on the temperature. They increase with the rising temperature, but the temperature dependency thereof varies from one material to another. The water-absorbing shrinkable yarns to be used in the side edge portions of disposable diapers have to function sufficiently even in the conceivable worst conditions of use. Therefore, (A) When the ambient temperature is taken into consideration, it is required that the initial performance characteristics required to be displayed instantaneously upon absorption of water, including the shrinkage percentage upon water absorption, rate of shrinkage, shrinkage stress and rate of shrinkage stress appearance should be exhibited even in the neighborhood of 20° C., which is considerably lower than the body temperature and (B) Those performance characteristics that are to be retained after water absorption and shrinkage (in particular rubber-like elasticity and strength) should be exhibited for a prolonged period of time even in the temperature range almost reaching the body temperature; any significant stress relaxation should not be observed.

In view of the above, the water-absorbing shrinkable yarns to be used in the side edge portions of disposable diapers should desirably have the following characteristics:

(1) Shrinkage percentage upon absorption of water: The maximum shrinkage in water at 20° C. (hereinafter referred to as "shrinkage upon water absorption" for short) should preferably amount to 30% or more, and the time required for reaching 30% shrinkage (hereinafter referred to as "rate of shrinkage upon water absorption") should be not longer than 10 seconds. When the shrinkage upon water absorption is less than 30%, the side edge portions may possibly fail to come into sufficiently close contact with the thigh.

(2) Shrinkage stress upon absorption of water: When the yarn size and economic features are also taken into consideration, the shrinkage stress in the original length state in water at 20° C. (hereinafter referred to as "shrinkage stress upon water absorption") should preferably amount to at least 30 mg/dr and the time required for the shrinkage stress of 30 mg/dr to appear upon water absorption (hereinafter referred to as "rate of shrinkage stress appearance upon water absorption") should preferably be not longer than 10 seconds. When the shrinkage stress upon water absorption is low, the force to bring the side edge portions of disposable diapers into close contact with the thigh is insufficient, so that shrinkage takes place only after softening of the side edge portions as a result of water absorption by the whole material constituting said portions, hence too late. It is possible to increase the shrinkage stress by increasing the size of the yarns to be used but, in this case, the protrusions formed by the shrinkable yarns make users feel unpleasant. Such measure is not preferable from the economy standpoint, either.

(3) The yarns after water absorption and shrinkage should have rubber-like elasticity. More specifically, the shrinkage stress in the water-containing state after 16 hours of immersion in water at 20° C. in the 30% shrinkage condition relative to the original length (hereinafter referred to as "shrinkage stress after water absorption") should preferably amount to 10 mg/dr or more. It is more preferable that the shrinkage stress in the water-containing state after 8 hours of immersion in water at 35° C. (hereinafter referred to as "shrinkage stress after water absorption at 35° C.") should be not less than 10 mg/dr. If the shrinkage stress after water absorption in the temperature range from 20° C. to the neighborhood of the body temperature decreases during use, the side edge portions of disposable diapers will fail to stretch and shrink according to the movement of users, hence will fail to remain in sufficiently close contact with the thigh. When the size of the yarns to be used is increased for increasing the shrinkage stress after water absorption, unfavorable results will be produced for the same reasons as mentioned above under (2).

(4) Strength after water absorption and shrinkage: This means the tensile strength at break in the water-containing state after 16 hours of immersion in water at 20° C. in the state of 30% shrinkage relative to the original length (hereinafter referred to as "strength after water absorption") and should preferably be not less than 300 mg/dr. This is because care should be taken so that even after shrinkage and swelling with water of the water-absorbing shrinkable yarns under abnormal conditions of wear of disposable diapers, the yarns cannot be broken as a result of vigorous movements of users.

In the above, the characteristics required in the case of water-absorbing shrinkable yarns for disposable diapers have been described taking said case as an example. These characteristics are also useful in applying the water-absorbing shrinkable yarns in other fields of use such as mentioned above. For instance, when the water-absorbing shrinkable yarns according to the second invention, which have the above-mentioned performance characteristics are used as fastening strings, root-binding materials or ham netting or fastening strings, the work efficiency can be much increased. When they are used as materials for making water roll coverings for use in offset printers, the covering exchange efficiency can be markedly enhanced. When they are used as moisture sensors, data with higher sensitivity can be obtained.

The second invention has thus successfully raised the above-mentioned four characteristics to higher functionality levels by making efficient use of the respective advantages of the rapidly shrinking fiber and slowly shrinking fiber and by alloting extended roles to them, as mentioned above. In other words, the fiber rapidly shrinking upon absorption of water is allowed to exhibit the initial stage characteristics (rate of shrinkage upon water absorption and rate of shrinkage stress appearance upon water absorption) upon absorption of water, while the performance characteristics to be persistent after absorption of water (shrinkage stress after water absorption, shrinkage stress after water absorption at 35° C. and strength after water absorption) are allotted to the fiber capable of absorbing water but capable of shrinking at a later time (generally within 5 minutes) as compared with the fiber capable of shrinking rapidly upon absorption of water. As will be evident from the above, it is desirable that the fiber rapidly shrinking upon water absorption and the fiber slowly shrinking upon water absorption, which constitute the second invention, should preserve the above-mentioned four characteristics in the combined state. For this purpose, the respective fibers should preferably have such performance characteristics as shown below in Table 1. Referring to the table, the capacity of the fiber rapidly shrinking upon water to hold the shrinkage stress at 30% shrinkage as determined at 5 minutes after water absorption is required for said fiber to bear its share of the shrinkage stress until the fiber slowly shrinking upon water absorption displays shrinkage stress (generally within about 5 minutes). Some data for a fiber substantially incapable of shrinking upon absorption of water are also given in Table 1.

TABLE 1

| | Fiber rapidly shrinking upon water absorption | Fiber slowly shrinking upon water absorption | Fiber substantially incapable of shrinking upon water absorption |
| --- | --- | --- | --- |
| Shrinkage upon water absorption | >30% | >30% | <10% |
| Rate of shrinkage upon water absorption | <10 sec | 10 sec to 5 min | — |
| Shrinkage stress upon water absorption | >150 mg/dr | >50 mg/dr | — |
| Rate of shrinkage stress appearance upon water absorption | <10 sec (at time of arrival at 150 mg/dr) | 10 sec to 5 min (at time of arrival at 50 mg/dr) | — |
| Shrinkage stress at 30% shrinkage upon water absorption | >30 mg/dr | >5 mg/dr | |
| Shrinkage stress retaining capacity at 30% shrinkage upon water absorption | >20 mg/dr | >5 mg/dr | |
| Shrinkage stress after water absorption | | >5 mg/dr | |
| Shrinkage stress after water absorption at 35° C. | | >5 mg/dr | |
| Strength after water absorption | | >500 mg/dr | |

The measurement methods for these performance characteristics are described later herein.

The above table clearly indicates that the rapidly shrinking fiber according to the first invention is quite suited as the above-mentioned fiber rapidly shrinking upon water absorption.

The polymers which constitute the fiber rapidly shrinking upon water absorption and the fiber slowly shrinking upon water absorption, which preferably have the characteristics given in Table 1, are, for example, polyvinyl alcohol, carboxy-containing modified polyvinyl alcohol, hydrolyzed polyacrylonitrile (with the nitrile group converted to —COOX where X is Li, K, Na, NH$_4$, or the like), carboxymethylated cellulose, and cellulose modified by grafting of acrylic acid.

In the following, the fiber rapidly shrinking upon water absorption and the fiber slowly shrinking upon water absorption are further described, taking particularly preferred polyvinyl alcohol type fibers as typical examples.

A. Fiber rapidly shrinking upon water absorption

The above-mentioned rapidly shrinking fiber according to the first invention is used.

B. Fiber slowly shrinking upon water absorption

In Japanese Laid-Open Patent Publication No. 60-2709, the present inventors have proposed a yarn which is made of ordinary PVA and capable of highly shrinking in water. The gist consists in promoting molecular orientation within the fiber as far as possible in an inhomogeneous state while controlling crystallization to a minimum necessary level so that inhomogeneous strain latent in the fiber inside can be relaxed by slight swelling action at the moment of its coming into contact with water and the change in state taking place in this process can be utilized in the water-absorbing shrinkable yarn. As is described in Japanese Laid-Open Patent Publication No. 60-2709, this fiber is characterized in that it shrinks by 10–60% within 30 seconds at a water temperature of 30°–40° C. When determined in water at 20° C., the rate of shrinkage upon water absorption is 40 seconds or more and the rate of shrinkage stress appearance amounts to 45 seconds or more. In addition, the shrinkage stress after water absorption is about 10 mg/dr, the shrinkage stress after water absorption at 35° C. is about 12 mg/dr and the strength after water absorption is 1.0 g/dr or more. With these two aspects, the fiber meets the requirements of the second invention and generally can be used favorably in the practice of the second invention.

Although the method of producing such fiber is detailedly described in the above-cited publication, it is again described in the following.

Starting material PVA: Ordinary PVA having a polymerization degree of 1,200–3,000 and a saponification degree of 98.0 mole percent or more Spinning: Wet spinning Drawing and heat treatment after spinning: Drawing is performed in a ratio of 4 or more at a temperature not higher than 130° C. while the fiber contains a salt and water. Heat treatment is conducted under tension so that a maximum shrinkage temperature of fiber being 65°–80° C. and a maximum shrinkage of fiber being 50% or more can be obtained. The maximum shrinkage temperature and maximum shrinkage percentage can be altered at will by altering the drawing ratio and drawing and heat treatment temperatures.

The fiber obtained by such method can be preferably used in the practice of the second invention. It is to be noted, however, that such fiber can of course be produced by some method other than the method just mentioned above.

In accordance with the second invention, the fiber rapidly shrinking upon water absorption (herein sometimes referred to as "rapidly shrinking fiber") and the slowly shrinking fiber are combined. A yarn made by mix twisting a fiber shrinking upon water absorption and a fiber substantially incapable of shrinking upon water absorption is known. As mentioned hereinabove, FIG. 1 schematically shows the state of a fiber (1) shrinking upon water absorption and of a fiber (2) substantially incapable of shrinking upon water absorption in a mix-twisted yarn and FIG. 2 the state of each fiber after allowing this twisted union yarn to absorb water and shrink. FIG. 3 schematically illustrates the state of a fiber (3) rapidly shrinking upon water absorption and of a fiber (4) slowing shrinking upon water absorption in a mix-twisted yarn according to the second invention, and FIG. 4 the state of each fiber after allowing this mix-twisted yarn to absorb water and shrink. Upon water absorption, the twisted yarn of the combination shown in FIG. 1 shrinks to take the form shown in FIG. 2. Thus, the fiber shrinking upon water absorption alone shrinks while the fiber incapable of shrinking upon water absorption is merely winding around the former.

Figure 2:
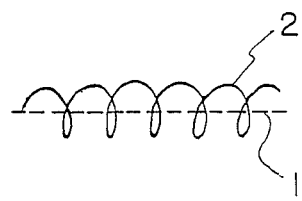
FIG. 2 is a schematic representation of the yarn shown in FIG. 1 in its shrunken state.
Figure 3:
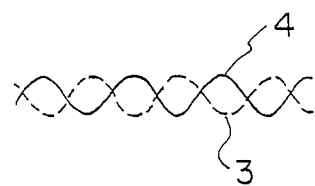
FIG. 3 is a schematic representation of a yarn made by twisting together a rapidly shrinking fiber (3) and a fiber (4) shrinking slowly upon absorption of water, namely a yarn according to the second invention.

The shrinkage stress in the twist yarn now having the form as shown in FIG. 2 as a result of water absorption and shrinkage is solely due to the water-absorbing shrinkable yarn, as can be seen in FIG. 2, and therefore the shrinkage stress will disappear once the water-absorbing shrinkable fiber undergoes stress relaxation (i.e. the shrinkage stress after water absorption will become insufficient). This drawback can indeed be avoided, as mentioned hereinabove, by giving twist to a much greater number of twist than the number of twist, that is necessary for uniting the two fiber species, to thereby inhibit swelling, but this measure causes remarkable decrease in rate of shrinkage upon absorption of water and in rate of shrinkage stress appearance upon absorption of water. The strength after water absorption is at any rate maintained by the fiber incapable of shrinking.

Japanese Laid-Open Patent Publication No. 57-11231 describes a mix-twisted yarn made of a fiber capable of shrinking upon absorption of water and a fiber substantially incapable of shrinking upon absorption of water. A check experiment conducted by the present inventors revealed that although it has apparently satisfactory functionality with a shrinkage stress after water absorption of 12 mg/dr, said mix-twisted yarn is subject to rapid stress relaxation at relatively high temperatures. For example, the shrinkage stress upon absorption of water at 35° C. is relaxed to 4 mg/dr or less (mere immersion in water at 35° C. for 2 hours in the state of 30% shrinkage relative to the original length leads to relaxation to 5 mg/dr) and, in such case, rubber-like elasticity cannot be displayed any more. Furthermore, for said mix-twisted yarn, the rate of shrinkage stress appearance upon water absorption is 20 seconds. Thus said yarn can hardly be regarded as having sufficient performance characteristics for its use in disposable diapers as a water-absorbing shrinkable yarn.

Figure 4:
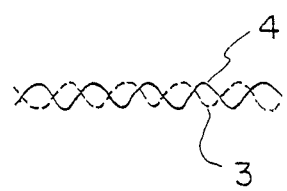
FIG. 4 is a schematic representation of the yarn shown in FIG. 3 in its shrunken state.

On the contrary, the twisted yarn according to the second invention (FIG. 3) takes a form similar to that shown in FIG. 2 temporarily in the very early stage of shrinkage due to absorption of water (generally in the earliest 10-second to 5-minute period as shown in Table 1) but then the shrinkage of the slowly shrinking fiber follows, so that the yarn takes such a form as shown in FIG. 4. As is clear from FIG. 4, the rapidly shrinking fiber and the slowly shrinking fiber in the water-absorbing shrinkable yarn according to the invention are both responsible for the occurrence of shrinkage stress and, even after the lapse of a long period, when the shrinking stress within the rapidly shrinking fiber is lost due to swelling, the slowly shrinking fiber still bears the responsibility for shrinkage stress to give a high shrinkage stress value. Moreover, as mentioned above, the shrinkage stress after water absorption is much greater than the sum of the shrinkage stress after water absorption or shrinkage stress after water absorption at 35° C. due to the yarn capable of rapidly shrinking upon absorption of water and that due to the yarn capable of slowly shrinking upon absorption of water. In addition, the strength after water absorption is sufficiently high.

Mere combination of a fiber rapidly shrinking upon water absorption and a fiber slowly shrinking upon water absorption cannot give the characteristics obtainable in accordance with the second invention. It is necessary that these fibers should be united together by mix-twisting or mix-spinning. Furthermore, for making the most of the rate of shrinkage upon water absorption and rate of shrinkage stress appearance characteristics possessed of the fiber capable of rapidly shrinking upon absorption of water without deterioration thereof by using such fiber capable of rapidly shrinking upon absorption of water, the number of twists to be employed when said fiber is combined with a fiber capable of slowly shrinking upon absorption of water is an important factor. When the number of twists is greater, the rate of shrinkage of the yarn upon absorption of water and the rate of shrinkage stress appearance upon absorption of water decrease. Investigations by the present inventors in search of an appropriate number of twists have revealed that for obtaining a fiber having those performance characteristics which meet the requirements of the second invention, the angle $\theta$ formed by the rapidly shrinking fiber with the lengthwise direction of the water-absorbing shrinkable yarn (hereinafter referred to as "twist angle $\theta$"; the method of determining the same to be mentioned later herein) should preferably be lower than 18°. Therefore, the water-absorbing shrinkable yarn according to the second invention should preferably be used after twisting to a number of twists which is less than 18° but is sufficient to unite the fibers. When the number of twist is higher, other problems such as mentioned below may possibly be encountered in addition to the above disadvantages:

A: Snarling takes place in the twisted yarn state and causes troubles such as yarn breakage in the step of incorporating the twisted yarn into edge portions of disposable diapers or in the weaving or knitting step, hence the rate of operation in the production process is reduced.

B: When the yarn absorbs water and shrinks, the yarn assumes a kinked state, so that uniform shrinkage can hardly be obtained.

Figure 5:
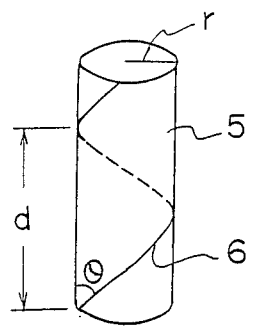
FIG. 5 is a schematic representation of the state of a single rapidly shrinking fiber (6) in a water-absorbing shrinkable yarn (5) according to the second invention, wherein r is the radius of the water-absorbing shrinkable yarn, d is the pitch of twist and $\theta$ is the twist angle.
Figure 6:
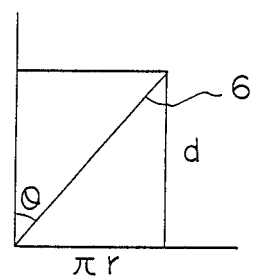
FIG. 6 is a development of FIG. 5.

As mentioned above, the twist angle $\theta$ represents the angle $\theta$ formed by the rapidly shrinking single fiber among the constituents of the water-absorbing shrinkable yarn with the lengthwise direction of the water-absorbing shrinkable yarn. As regards the value of said angle, the value obtained by calculation using the formula given below is used. FIG. 5 is a schematic representation of the state of the rapidly shrinking fiber component 6 twisted to a twist angle $\theta$ in a water-absorbing shrinkable yarn (yarn diameter r cm, pitch of twist d cm) and FIG. 6 is a developed view of the same. As will be easily understood from FIG. 5 and FIG. 6, the twist angle $\theta$ is determined in the following manner. Here it is assumed that the yarn is a perfect cylinder. Gaps among single fibers are disregarded. Pitch of twist d: 2.54/T (cm) (T: number of twist expressed in t/in)

$$\text{Radius } r = \sqrt{\frac{dr}{\pi \times \rho \times 900000}} \text{ (cm)}$$

dr: Fineness based on corrected weight of the water-absorbing shrinkable yarn $\rho$: Density of the water-absorbing shrinkable yarn (in the case of a mix-spun or mix-twisted yarn made of different fibers, $\rho$ is a weighted average) The following $\rho$ values are to be used: 1.26 for PVA fibers, 1.54 for cotton, 1.50 for rayon, and 1.15 for polyacrylonitrile.

$\theta(°)$ is calculated using $$\theta = \tan^{-1} \frac{\pi r}{d}.$$

It is assumed that the single fibers do not pass along the outer surface of the yarn but pass the points at ½×2πr.

Figure 7:
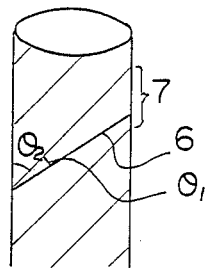
FIG. 7 is a schematic representation of a single rapidly shrinking fiber in a water-absorbing shrinkable yarn according to the second invention which is a fold-twisted yarn with the primary twist and final twist made in the same direction, wherein 7 is the primary twist yarn, 6 is the single rapidly shrinking fiber, $\theta_1$ is the twist angle of the single rapidly shrinking fiber in the primary twist yarn and $\theta_2$ is the twist angle of the primary twist yarn in a folded yarn.

When the water-absorbing shrinkable yarn is constructed by rapidly shrinking fibers in a folded yarn, the twist angle $\theta_1$ of the rapidly shrinking fiber in the primary twist yarn and the twist angle $\theta_2$ of the final twist yarn in the folded yarn are calculated individually using the above formula. When the primary twist and the final twist are in the same direction (cf. FIG. 7), then $\theta = \theta_1 + \theta_2$ and when the primary twist and the finary twist are in opposite directions, then $\theta = \theta_1 - \theta_2$.

A singular phenomenon has been Confirmed such that, for unknown reasons, the shrinkage stress after water absorption and the shrinkage stress after water absorption at 35° C. of a twisted yarn obtained by twisting together a fiber capable of rapidly shrinking upon water absorption and a fiber capable of slowly shrinking upon water absorption are twice or more greater than the sum of the shrinkage stress after water absorption values given by the respective original yarns and the sum of the shrinkage stress after water absorption at 35° C. values given by the respective original yarns, respectively.

In uniting them together, the fiber capable of rapidly shrinking upon water absorption and the fiber capable of slowly shrinking upon water absorption may have the forms filament+filament, filament+spun yarn, spun yarn+filament, or spun yarn+spun yarn. They are used in the twisted state generally at a twist angle of not more than 18°, as mentioned above. Both the fibers may also be mixed on the occasion of spinning. It is further possible to blend them in the opening and picking stage or sliver forming stage or make them up into the so-called core spun yarn.

Of course this water-absorbing shrinkable yarn can be used as it is in the cord-like form or be processed to a woven fabric or knitted fabric form depending on the purpose of use thereof.

The third aspect of the present invention is now described in further detail.

The third invention provides a water-absorbing shrinkable material having a strip-like form which is characterized in that it is composed of a nonwoven fabric capable of shrinking upon absorption of water and a specific yarn (rapidly shrinking yarn) capable of shrinking upon water absorption at a higher rate and to a greater extent as compared with said nonwoven fabric with said yarn united with said nonwoven fabric. When this water-absorbing material is used in the lengthwise edge portions of disposable diapers, disposable diapers relatively free of the risk of leakage of urine and so forth and of the risk of causing impressions of constriction on the thigh.

Furthermore, the water-absorbing shrinkable material according to the third invention should preferably have the following characteristics:

(a) When measured in water at 20° C., the maximum shrinkage percentage in the lengthwise direction should preferably be not less than 30%, the time required for the lengthwise shrinkage to reach 30% not longer than 20 seconds, the shrinkage stress in the original length state not less than 100 g, and the time required for the shrinkage stress of 100 g to appear not longer than 20 seconds. When a water-absorbing shrinkable material insufficient in these initial characteristics concerned with the shrinkage upon absorption of water is used in the diaper side edge portions, leakage sometimes takes place.

(b) When measured after 8 hours of immersion in water at 20° C. in the state of 30% shrinkage in the lengthwise direction, the shrinkage stress in the wet condition should preferably be not less than 30 g and the tensile strength at break not less than 1 kg. If these characteristics to be retained after water absorption are insufficient, the diapers with said water-absorbing shrinkable material incorporated therein will not be able to expand and shrink to an extent sufficient to respond to the movements of wearers, so that the closeness in contact with the thigh will become insufficient or the said shrinkable material will break upon violent movements of wearers, as the case may be.

(c) The nonwoven fabric capable of shrinking upon absorption of water should preferably be able to absorb water at 20° C. in an amount of 200 g/m$^2$ and shrink by not less than 10% in the lengthwise direction in water at 20° C. and further should preferably have a weight of not less than 30 g/m$^2$. With nonwoven fabrics having a water absorbency of less than 200 g/m$^2$, there is the possibility of leakage of urine and so forth. Nonwoven fabrics having a weight of less than 30 g/m$^2$ sometimes cause occurrence of impression of constriction on the thigh. When nonwoven fabrics for which the lengthwise shrinkage percentage is less than 10% are used, gathers are sometimes formed on the nonwoven fabrics upon shrinkage of the water-absorbing shrinkable materials, causing the impressions of constriction.

In view of the necessity of providing water-absorbing shrinkable materials with sufficient initial characteristics and of the economic aspect, the rapidly shrinking yarn to be used in the above water/absorbing shrinkable material includes the rapidly shrinking fiber according to the first invention described hereinabove.

The most characteristic structural feature of the water-absorbing shrinkable material according to the third invention lies in that the material consists of a nonwoven fabric capable of shrinking upon absorption of water and a yarn capable of shrinking, upon absorption of water, at a higher rate and to a greater extent as compared with said nonwoven fabric, namely a rapidly shrinking yarn, as united with said nonwoven fabric. The means of uniting may include sewing the rapidly shrinking yarn into the nonwoven fabric (the rapidly shrinking yarn being used as the needle thread or bobbin thread or as both), knitting the rapidly shrinking yarn into the nonwoven fabric and needle-punching an assemblage of two nonwoven fabric sheets and the rapidly shrinking yarn interposed therebetween, among others. Among them most preferable is the sewing method from the viewpoints of processability and cost, among others.

The water-absorbing shrinkable material according to the third invention is very useful not only as a material for use in the side edge portions of disposable diapers but also as a blood-absorbing material for use in case of bleeding, a tourniquet, or a first-aid treatment material for immobilizing the affected part in case of fracture, for instance.

Figure 8:
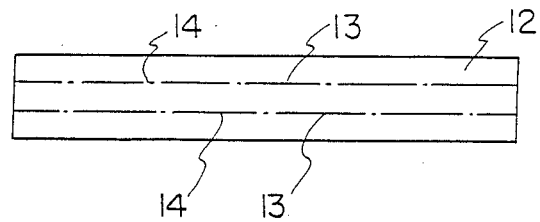
FIG. 8 is a plan view of an exemplary water-absorbing shrinkable material according to the third invention.
Figure 9:
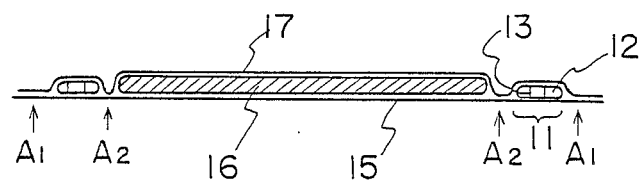
FIG. 9 is a cross-sectional view of an exemplary disposable diaper in which a water-absorbing shrinkable material according to the third invention is used.
Figure 10:
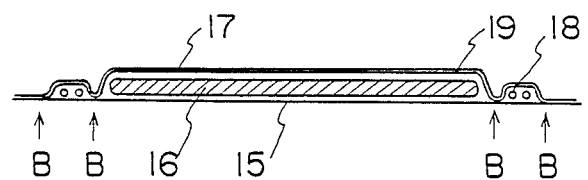
FIG. 10 is a cross-sectional view of an exemplary conventional disposable diaper.

For further illustrating the third invention, FIG. 8 and FIG. 9 are referred to.

In FIG. 8, an example of the water-absorbing shrinkable material according to the third invention is shown. In this example, the rapidly shrinking yarn is united with the nonwoven fabric by sewing the former into the latter. In FIG. 8, a water-absorbing shrinkable nonwoven fabric is indicated by 12, a rapidly shrinking yarn by 13 and a polyester sewing thread by 14. While the third invention enables the production of disposable diapers using the above water-absorbing material as an auxiliary absorbent without requiring contact thereof with the water absorbent and without requiring any means of water transfer, an example of such diaper is shown in FIG. 9, wherein the diaper comprises a back sheet 15 made of a polyethylene film about 25 μm in thickness, a water absorbent 16 for absorbing urinary water or the like, a surface sheet 17 and a water-absorbing shrinkable material 11 capable of functioning also as an auxiliary absorbent. In the figure, the surface sheet and the back sheet are adhered together at the sites $A_1$ and $A_2$ by heat sealing or some other means so that the shrinkage of the water-absorbing shrinkable material can take place uniformly in the side edge portions. As is clear from FIG. 9, the water-absorbing shrinkable material 11 is disposed in the edge portions of disposable diapers preferably without contacting with the water absorbent 16. The use of a means of transferring water is unnecessary between the water absorbent 16 and the water-absorbing shrinkable material 11.

The following are the characteristic features of the water-absorbing shrinkable material according to the third invention and of disposable diapers in which said water-absorbing shrinkable material is used.

(i) Impressions caused by constriction are not formed on the thigh.

While the water-absorbing shrinkable yarns so far used in disposable diapers are yarn-like materials about 0.5–0.7 mm in thickness, the water-absorbing shrinkable material according to the third invention comprises a nonwoven fabric and the rapidly shrinking yarn united together, as mentioned hereinabove. Said water-absorbing shrinkable material thus undergoes planar shrinkage and comes into close contact with the thigh, so that no or almost no impressions of constriction are formed on the thigh.

(ii) Leakage from side edge portions does not occur.

One constituent element of the water-absorbing shrinkable material according to the third invention is a nonwoven fabric which can function as an auxiliary absorbent and the time required for the water-absorbing shrinkable material according to the third invention to shrink is very short. As a result of cooperation of these effects, water cannot leak out of diapers from the side edge portions even when water exudes in large quantities from the water absorbent toward said side edge portions.

(iii) Stuffiness is hardly caused.

As already mentioned in the description of the prior art, disposable diapers of the type (a) are always kept in close contact with the thigh from the time of putting on to the time of taking off, so that stuffiness easily results. Conventional disposable diapers of the type (b) have a structure such that water of initial urination after putting them on is led to a water-absorbing shrinkable yarn in a stage as early as possible by such means of water transfer as absorbent paper. In the early stage of wearing when no urination has occurred yet, the side edge portions are loose but, after urination, the side edge portions come into and remain in close contact with the thigh. On the contrary, in those disposable diapers in which the water-absorbing shrinkable material according to the third invention is used, the water-absorbing shrinkable material comprises, as one constituent element thereof, a nonwoven fabric, preferably a nonwoven fabric having an absorbency of not less than 200 g/m². Owing to its ability to absorb water, the nonwoven fabric can function as an auxiliary water absorbent, so that a structure can be employed such that shrinkage occurs for the first time upon exudation of the water once absorbed in a water absorbent to the water-absorbing shrinkable material. Therefore, when such structure is employed, the time between putting on and shrinkage can be prolonged substantially and, as a result, stuffiness can very hardly be caused.

The constitution of the water-absorbing shrinkable material according to the third invention is described in further detail in the following.

(i) Constitution of the nonwoven fabric

The nonwoven fabric which is a constituent of the water-absorbing shrinkable material according to the third invention should preferably be able to absorb water at 20° C. in an amount of not less than 200 g/m² and show a self-shrinkage percentage of not less than 10% in the lengthwise direction upon absorption of water at 20° C. Furthermore, it should preferably show a shrinkage of not less than 30% in the lengthwise direction when assisted by an external force (when united with the rapidly shrinking yarn). Nonwoven fabrics having a water absorbency of less than 200 g/m² are somewhat insufficient in the function of absorbing the exudate water coming from the water absorbent of a disposable diaper to the side edge portions (namely the function as an auxiliary water absorbent) and, in some instances, allow leakage from the side edge portions. Nonwoven fabrics showing a self-shrinkage percentage of less than 10% in the lengthwise direction upon absorption of water cannot become soft to a sufficient extent at the time of water absorption, but may reduce the shrinkage characteristics (shrinkage percentage, rate of shrinkage, shrinkage stress, rate of shrinkage stress appearance) of the rapidly shrinking yarn united therewith to thereby cause insufficiency in the functionality as water-absorbing shrinkable materials, as the case may be. Furthermore, since such nonwoven fabrics are rough and rigid even after water absorption and shrinkage, wrinkles are formed thereon and may cause congestion and leakage.

Furthermore, said nonwoven fabric should preferably have a weight of not less than 30 g/m², more preferably not less than 40 g/m². When the weight is less than 30 g/m², the function to receive, on a plane, the shrinkage occurring in the rapidly shrinking yarn and distribute the same in the transverse direction becomes insufficient. In such case, impressions caused by constriction may be formed on the thigh.

It is of course possible to merely fold up a nonwoven fabric having a weight of less than 30 g/m² or a water absorbency of less than 200 g/m² or pile up two or more such nonwoven fabrics to give an aggregate nonwoven fabric having a weight of not less than 30 g/m² and a water absorbency of not less than 200 g/m². Such aggregate nonwoven fabric can be used effectively as well. It is further possible to merely fold up a nonwoven fabric having a weight less than 30 g/m² or a water absorbency of less than 200 g/m² as united with the rapidly shrinking yarn or pile up two or more such nonwoven fabric with the rapidly shrinking yarn united therewith. Thus, the nonwoven fabric so referred to herein includes multilayer nonwoven fabrics without particular interlayer adhesion, too.

The nonwoven fabric capable of absorbing water at 20° C. in an amount of not less than 200 g/m² and showing a lengthwise self-shrinkage of not less than 10% in water at 20° C. can be obtained, for example, in the following manner. The raw stock to be used is a fiber made of a hydrophilic polymer and showing a shrinkage percentage of not less than 10% in water at 20° C. As the most preferable representative of such fiber, there may be mentioned the fiber described in the above-cited Japanese Laid-Open Patent Publication No. 60-2709. The fiber described in this publication shows a shrinkage percentage of about 35% in water at 20° C.

In the addition to the above fiber, fibers made of hydrolyzed polyacrylonitrile (with the nitrile group converted to —COOX wherein X is Li, K, Na, $NH_4$, etc.), carboxymethylated cellulose or acrylic acid-grafted cellulose, for instance, may suitably be used as well.

The nonwoven fabric to be used in the practice of the third invention is produced by the dry method using such fiber mainly. A web taken out of a card or a random webber is converted to a nonwoven fabric by ordinary needle punching or by a technique of causing nonwoven fabric-constituting fibers themselves to form a knit on the surface of the web (the so-called arachne technique) and/or by heat treatment for the case where the web contains a heat-meltable fiber (binder fiber). Although it is possible to produce a nonwoven fabric by using a resin binder in place of performing needle punching, the nonwoven fabric produced in that case tends to show a decreased selfshrinkage percentage and a decreased water absorbency due to adhesion of the resin binder to the surface of each single fiber constituting the nonwoven fabric. Therefore, the needle punching, heat fusion and arachne techniques are preferred.

The nonwoven fabric should preferably have a thickness of 0.5 mm to 3 mm. The nonwoven fabric thickness can be adjusted not only by adjusting its weight but also by adjusting the frequency of needle punching or calendering after nonwoven fabric production.

Said nonwoven fabric may contain the so-called binder fiber, which is heat meltable, as mentioned above. In cases where the nonwoven fabric contains a heat-meltable binder fiber, direct adhesion thereof with the back sheet and the surface sheet (sheets indicated by 15 and 17 in FIG. 9) can be employed as the means of incorporating the water-absorbing shrinkable material into disposable diapers. When the nonwoven fabric does not contain any heat-meltable binder fiber, a method is also employable which comprises sewing the rapidly shrinking yarn to be mentioned later herein into said nonwoven fabric with a polyethylene sheet superposed on said nonwoven fabric and heat-sealing said polyethylene sheet with the back sheet and the surface sheet.

The water absorbency of the nonwoven fabric can be modified by adjusting the weight or tightness of the nonwoven fabric, the frequency of needle punching, and so forth.

(ii) Rapidly shrinking yarn

As the rapidly shrinking yarn which is one consituent of the third invention, there may be used a yarn made of the rapidly shrinking fiber according to the first invention. When made up into a yarn having an appropriate thickness and then united with the water-absorbing shrinkable nonwoven fabric, such rapidly shrinking fiber can display the initial and lasting performance characteristics required of the water-absorbing shrinkable material for use in the edge portions of disposable diapers. Furthermore, the water-absorbing shrinkable yarn according to the second invention can suitably be used as well.

Other yarns that contain the rapidly shrinking fiber according to the first invention and have desired performance characteristics can also be used as the rapidly shrinking yarns constituting the third invention. The rapidly shrinking yarn should preferably have a thickness of 200–5,000 dr from the viewpoint of prevention of occurrence of impressions of constriction on the thigh.

(iii) Method of uniting the nonwoven fabric with the rapidly shrinking yarn

The incorporation of the rapidly shrinking yarn in the nonwoven fabric can be accomplished by sewing on a sewing machine using the rapidly shrinking yarn as the needle thread or bobbin thread or as both. The sewing is carried out preferably in the manner of lock-stitching and the seam pitch is preferably 1–10 mm. When the rapidly shrinking yarn is used either as the needle thread or as the bobbin thread, the other thread may not always be a yarn capable of shrinking upon absorption of water but may be a sewing thread which has flexibility and is made of a natural, chemical or synthetic fiber and in use in the production of ordinary clothing items or as an industrial material, such as a cotton yarn, a polyester yarn, an ordinary PVA yarn or a nylon yarn. The thickness of this sewing thread is not critical but, when the conditions of use of disposable diapers and economic features are taken into consideration, those threads that are relatively fine and have a sewing thread number of 60–100 are preferred.

The rapidly shrinking yarn and the water-absorbing shrinkable nonwoven fabric can be united together also by knitting using the rapidly shrinking yarn as the knitting yarn. Thus, the rapidly shrinking yarn and the water-absorbing shrinkable nonwoven fabric can be united together by knitting the rapidly shrinking yarn into the nonwoven fabric which is either produced simultaneously with the knitting or fed after production thereof in advance. In this case, the pitch interval) for the warp is preferably 3–10 mm, and the number of courses is preferably 3–25/in.

In addition to the above methods, needle punching two water-absorbing nonwoven fabric sheets and the rapidly shrinking yarn sandwiched therebetween can also accomplish the purpose of uniting the nonwoven fabric and the rapidly shrinking yarn together. Any other method of uniting than those mentioned above may be used as far as appropriate.

The thus-obtained assemblage of the rapidly shrinking yarn and the water-absorbing shrinkable nonwoven fabric is slit to a width of 5 mm to 4 cm, preferably 1–3 cm, to give a rapidly shrinking material in the tape form. The water-absorbing shrinkable material should preferably have at least two rows of the rapidly shrinking yarn. For the rapidly shrinking yarn to fully display its shrinking ability, it is preferable that said yarn should be united in the lengthwise direction of the tape-shaped water-absorbing shrinkable material. Of course this means not only the state in which the rapidly shrinking yarn is united in a straight line with the nonwoven fabric in the lengthwise direction of said fabric but also any state in which the rapidly shrinking yarn is united with the nonwoven fabric in a manner such that the shrinkage of said yarn can contribute to the lengthwise shrinkage of the water-asborbing shrinkable material. The water-absorbing shrinkable material having the above constitution must function effectively as a water-absorbing shrinkable material in the side edge portions of disposable diapers. When every condition of use of disposable diapers is taken into consideration, said material should preferably have the following performance characteristics.

(i) Shrinkage percentage upon water absorption: The maximum lengthwise shrinkage in water at 20° C. (shrinkage percentage upon water absorption) should preferably be not less than 30%, and the time required for the shrinkage to reach 30% (rate of shrinkage upon water absorption) not longer than 20 seconds. When the shrinkage percentage upon water absorption is less than 30%, there is the possibility that the material fail to come into close contact with the thigh of wearers. The shrinkage percentage upon water absorption and the rate of shrinkage upon water absorption largely depend on those of the rapidly shrinking yarn and further on the shrinkage percentage of the nonwoven fabric. A nonwoven fabric with a shrinkage percentage upon water absorption of less than 10% is not preferable.

(ii) Shrinkage stress upon water absorption: The shrinkage stress in water at 20° C. in the original length state (shrinkage stress upon water absorption) should preferably be not less than 100 g, and the time required for the shrinkage stress of 100 g to appear upon absorption of water (rate of shrinkage stress appearance upon water absorption) not longer than 20 seconds. When the shrinkage stress upon water absorption is lower, the force for maintaining the side edge portions of disposable diapers in close contact with the thigh becomes insufficient and this sometimes leads to leakage. The shrinkage stress upon water absorption and the rate of shrinkage stress appearance upon water absorption are mostly dependent on those of the rapidly shrinking yarn.

(iii) Shrinkage stress after water absorption: The water-absorbing shrinkable material after water absorption and shrinkage should preferably have rubber-like elasticity and, more concretely, the shrinkage stress in the wet state after 8 hours of immersion in water at 20° C. in the state of 30% shrinkage relative to the original length (shrinkage stress after water absorption) should preferably be not less than 30 g. In case the shrinkage stress after water absorption decreases during use, the side edge portions of disposable diapers will become insufficient in the ability to stretch and shrink according to the movements of wearers, and the state of contact with the thigh will sometimes become worsened. The shrinkage stress after water absorption is almost dependent on that of the rapidly shrinking yarn but shows a higher value than that of the rapidly shrinking yarn since said yarn is in union with the nonwoven fabric.

(iv) Strength after water absorption and shrinkage: This means the tensile strength at break as determined in the wet state after 8 hours of immersion in water at 20° C. in the state of 30% shrinkage relative to the original length (strength after water absorption) and should preferably be not less than 1 kg. This requirement is put forth because care should be taken so that the water-absorbing shrinkable material cannot be broken even upon vigorous movements of wearers after shrinkage of the water-absorbing shrinkable material by 30% or more as a result of absorption of water in an abnormal condition of wearing of disposable diapers.

Disposable diapers in which such water-absorbing shrinkable material is used are now described. As mentioned hereinabove, the water-absorbing shrinkable material according to the third invention has ability to absorb water, and it is necessary for urinary water or the like absorbed by the water absorbent to migrate to said material only after said absorbent has become incapable of absorbing any further portion of such water. Therefore, any means of guiding water is needed between the water absorbent and the water-absorbing shrinkable material. Since such means is effective in a negative way, it is rather preferable that the water absorbent and the water-absorbing shrinkable material should not be in contact with each other. This is because the water-absorbing shrinkable material functions as an auxiliary water absorbent, so that said material is required to start shrinkage only upon arrival thereat of urinary water or the like which is an exudate from the water absorbent. Earlier shrinkage of the water-absorbing shrinkable material may cause stuffiness. In the disposable diapers in which the water-absorbing shrinkable materil according to the third invention is used, there may be used an elastomer heretofore in use, such as polyurethane, combinedly.

The following are preferred forms of the water-absorbing shrinkable material according to the third invention and of the disposable diaper in which said shrinkable material is used but are by no means limitative of the present invention. Water-absorbing shrinkable material:

Nonwoven fabric: A nonwoven fabric made by subjecting a card web or a random web made of a fiber showing a shrinkage percentage of not less than 20% in water at 20° C. to needle punching to a weight of 40–80 g/m$^2$ and a thickness of 0.5–2 mm.

Rapidly shrinking yarn: A yarn produced by combinedly twisting one yarn made of the rapidly shrinking fiber according to the first invention (e.g. a 500 dr/72 f yarn made of a polyvinyl alcohol copolymer with 2 mole percent of itaconic acid) and one yarn capable of slowly shrinking upon absorption of water (e.g. a spun yarn having an English cotton yarn count of 10′ s/1, produced by spinning on a perlock system a tow obtained by wet spinning polyvinyl alcohol by the method described in the above-cited Japanese Laid-Open Patent Publication No. 60-2709) to 3.0 t/in (Z).

Water-absorbing shrinkable material: A water-absorbing shrinkable material produced by sewing the above rapidly shrinking yarn as the needle thread with a polyester sewing thread having a sewing thread number of 80 (cotton yarn number 80′ s/3) as the bobbin thread at a sewing pitch of 2–5 mm and a sewing interval of 3–5 mm, followed by cutting to a width of 10–15 mm. Each water-absorbing shrinkable material strip should preferably contain two or three rows of the rapidly shrinking yarn parallel to the lengthwise direction of said strip. The water-absorbing shrinkable material with the sewing threads incorporated therein should preferably have a thickness of 0.5–2 mm.

Disposable diaper: A disposable diaper made by fixing the above water-absorbing shrinkable material on the side edge portions without contacting said material with the water absorbent. Any means of leading water from the water absorbent to the water-absorbing shrinkable material is not used at all.

As detailedly mentioned hereinabove, the water-absorbing shrinkable material according to the third invention is used mainly in disposable diapers but, as mentioned hereinabove, it is usable also as a blood-absorbing material for use in case of bleeding, a tourniquet, or a first-aid treatment material for immobilizing the affected part in case of fracture.

The methods of measurement of the performance characteristics of the fiber and yarn which is provided or used in accordance with the first, second and third inventions mentioned above are described in detail in the following. The fiber and yarn to be tested (hereinafter collectively referred to as "fiber") are allowed to stand in advance in an atmosphere kept under standard conditions (20° C.±2° C., relative humidity 65±2%) to thereby cause them to reach moisture equilibrium and thereafter subjected to measurement under the standard conditions mentioned above.

1. Shrinkage percentage upon water absorption (i.e. maximum shrinkage percent in water at 20° C.) and rate of shrinkage upon water absorption The fiber is immersed in water at 20°±1° C. such that the fiber is laid under a load of 1 mg/dr in water, and the immersion time (in seconds) and the shrinkage percentage (relative to the original length) are measured. The time (in seconds) required for the shrinkage percentage to reach 30% is reported as the rate of shrinkage upon water absorption and the maximum shrinkage percentage attained within 5 minutes of immersion is reported as the shrinkage percentage upon water absorption.

2. Shrinkage stress upon water absorption and rate of shrinkage stress appearance The fiber is mounted on a constant rate extension type tensile tester at a grip interval of 10 cm under a tension of 5 mg/dr. Then, the fiber is immersed in water at 20°±1° C. and the shrinkage stress and the immersion time (in seconds) are measured correlatively while the grip interval is kept unchanged. The maximum shrinkage stress within 5 minutes of immersion is reported as the shrinkage stress upon water absorption (in mg/dr) and the time (in seconds) required for the shrinkage stress to reach 150 mg/dr (when the specimen is a rapidly shrinking fiber) or 50 mg/dr (when the specimen is a slowly shrinking fiber) or to reach 30 mg/dr (when the specimen is a water absorbing shrinkable yarn) as the rate of shrinkage stress appearance upon water absorption.

3. Shrinkage stress at 30% shrinkage upon water absorption and shrinkage stress retaining capacity at 30% shrinkage The fiber is mounted on a constant rate extension type tensile tester at a grip interval of 10 cm in a 30% slackened state relative to the original length. The fiber is then immersed in water at 20°±1° C. While maintaining the grip distance unchanged, the shrinkage stress and the immersion time (in seconds) are recorded correlatively. The maximum shrinkage stress value within 5 minutes of immersion in water is reported as the shrinkage stress at 30% shrinkage upon water absorption (in mg/dr) and the shrinkage stress after 5 minutes of immersion in water as the shrinkage stress retaining capacity at 30% shrinkage upon water absorption (in mg/dr).

4. Shrinkage stress after water absorption

In the same manner as in measuring the shrinkage stress at 30% shrinkage upon water absorption, the shrinkage stress after 16 hours of immersion is recorded and reported as the shrinkage stress after water absorption (in mg/dr).

5. Shrinkage stress after water absorption at 35° C.

In the same manner as in measuring the shrinkage stress after water absorption except that the water temperature is 35°±1° C. and the immersion time is 8 hours, the shrinkage stress after 8 hours of immersion is recorded and reported as the shrinkage stress after water absorption at 35° C. (in mg/dr).

6. Strength after water absorption

In the same manner as in measuring the shrinkage stress at 30% shrinkage upon water absorption, the specimen after 16 hours of immersion is tested in the wet state for tensile strength at break on a constant rate extension type tensile tester. An initial load of 5 mg/dr is laid on the specimen when it is fixed by the chucks.

7. Weight loss due to dissolution

The sample is cut to a length of about 10 mm. A 1- to 2-gram portion is sampled and dried and its bone dry weight ($W_o$ g) is measured accurately according to JIS L-1013. Then, the accurately weighed sample is dispersed in water at 20° C. in a bath ratio of 200 and, after 60 minutes of standing, the dispersion is filtered through a filter paper No. 5A, 11 cm in diameter, for quantitative determination. After cessation of water drop falling, the insoluble matter is dried and its bone dry weight (W g) is measured. The weight loss due to dissolution is calculated as follows:

$$\text{Weight loss due to dissolution} = \frac{W_o - W}{W_o} \times 100(\%)$$

The methods of measurement of the performance characteristics of the water-absorbing shrinkable material according to the third invention and the nonwoven fabric constituting said material are described in detail in the following. All the samples to be tested are allowed to stand in advance in an atmosphere kept under standard conditions (20°±2° C., relative humidity 65±2%) to thereby attain their moisture equilibrium. The measurements are carried out under the standard conditions specified above.

8. Shrinkage percentage upon water absorption and rate of shrinkage upon water absorption in water-absorbing shrinkable material The measurements are carried out in the same manner as mentioned above in 1.

9. Shrinkage stress upon water absorption and rate of shrinkage stress appearance upon water absorption in water-absorbing shrinkable material The measurements are carried out in the same manner as mentioned above in 2 except that the time (in seconds) required for the shrinkage stress to reach 100 g is reported as the rate of shrinkage stress appearance upon water absorption.

10. Shrinkage stress after water absorption in water-absorbing shrinkable material The water-absorbing shrinkable material is mounted on a constant rate extension type tensile tester at a grip interval of 10 cm in a 30% slackened state relative to the original length and then immersed in water at 20°±1° C. The shrinkage stress is measured after 8 hours of immersion with the grip interval kept constantly and reported as the shrinkage stress after water absorption (in g).

11. Strength after water absorption of water-absorbing shrinkable material

In the same manner as in measuring the shrinkage stress after water absorption for water-absorbing shrinkable materials, the sample after 8 hours of immersion in water is tested in the wet state for tensile strength at break using a constant rate extension type tensile tester. An initial load of 5 mg/dr is laid on the sample when it is fixed by the chucks.

12. Water absorbency of nonwoven fabric itself

A nonwoven fabric specimen 20-100 cm$^2$ in area is accurately measured for its area. Then the specimen is immersed in water at 20° C. for 5 minutes, then taken out of the water, laid on a wire netting horizontally, allowed to stand for 5 minutes to thereby allow the excess water to drop, and weighed, and the water absorption per square meter of the nonwoven fabric area before immersion is calculated.

13. Shrinkage percentage upon water absorption for nonwoven fabric itself

A strip-shaped specimen about 30 cm in length is taken from the nonwoven fabric in the lengthwise direction thereof, marked accurately to indicate a 20-cm interval, and immersed in water at 20° C. The immersion time (in seconds) and the shrinkage percentage (relative to the original length) are measured and the maximum shrinkage percentage within 5 minutes of immersion in water is reported as the shrinkage percentage upon water absorption.

14. Thickness of nonwoven fabric and water-absorbing shrinkable material

The thickness measurement is carried out using a dial gauge adjusted such that a load of 10 g/cm² is laid on the specimen.

solution was forced through a spinneret (0.1 mm$\phi$×72 holes) and the filaments thus spun were dried under the following conditions:

|  | Itaconic acid-modified PVA | Low saponification degree PVA |
|---|---|---|
| Spinning chimney temperature (cooling zone) | 30° C. | 30° C. |
| Spinning chimney temperature (predrying zone) | 110° C. | 110° C. |
| Cooling zone length | 0.25 m | 0.25 m |
| Predrying zone length | 2.35 m | 2.35 m |
| Drying temperature | 125° C. | 124° C. |

Each of the filaments thus dried had a moisture content of not more than 0.1%.

The thus-obtained filaments of the above two kinds were heat-treated at varied drawing oven temperatures at a constant drawing ratio of 5.5 and then tested for characteristic properties in water at 20° C. by the methods specified. The results obtained are shown in

TABLE 2

The filaments had a fineness of 680 dr/72 f.

|  | Drawing/heat treatment temperature | T1 | S1 | T2 | S2 | W1 | % Shrinkage upon water absorption |
|---|---|---|---|---|---|---|---|
| Example 1 | 200° C. | 3.8 | 0.2 | 2 | 0.05 | 18.5 | 55 |
| Example 2 | 210° C. | 4.0 | 0.2 | 3.5 | 0.04 | 7.9 | 50 |
| Comparative Example 1 | 170° C. | 3.7 | 0.3 | 2 | 0.06 | 61.5 | 67 |
| Comparative Example 2 | 180° C. | 3.8 | 0.3 | 2 | 0.05 | 49.1 | 65 |
| Comparative Example 3* | 190° C. | 144.0 | 0.4 | 155 | 0.07 | 4.1 | 32 |

T1: Time (in seconds) required for the shrinkage percentage reaches 30% (i.e. rate of shrinkage upon water absorption)
T2: Time (in seconds) required for the shrinking stress to reach 150 mg/dr in the original length state (i.e. rate of shrinkage stress appearance)
S1: Shrinkage stress in the original length state (g/d) (i.e. shrinkage stress upon water absorption)
S2: Shrinkage stress (g/d) in the state of the 30% shrinkage relative to the original length (i.e. shrinkage stress at 30% shrinkage upon water absorption)
W1: Weight loss due to dissolution (%)
*In Comparative Example 3, the low saponification degree PVA was used.
1 mg/dr = 1 × $10^{-6}$ kgf/dr
    = 9.80665 × $10^{-6}$ N/dr
    = 9.80665 × $10^{-1}$ dyne/dr
"g/d" is an abbreviation for "gram force per denier" and thus equals $10^3$ mg/dv.

Notes:
(i) In determining the load and initial tension to be applied to the water-absorbing shrinkable material, the total denier for the water-absorbing shrinkable yarn contained in the water-absorbing shrinkable material is used.
(ii) When the rapidly shrinking yarn is made of a composite of a rapidly shrinking fiber and some other material, the rapidly shrinking fiber alone is taken out for measurement.

EXAMPLES 1-2 AND COMPARATIVE EXAMPLES 1-3

These examples and comparative examples are concerned with the first invention.

Itaconic acid (2 mole percent)-modified PVA (average degree of polymerization 1,800 degree of saponification 97 mole percent) and low saponification degree PVA (average degree of polymerization 1,700; degree of saponification 98 mole percent) were each used to prepare a 50% aqueous PVA spinning solution. Each

EXAMPLES 3-7 AND COMPARATIVE EXAMPLES 4-7

These examples and comparative examples are concerned with the second invention.

(1) Production of rapidly shrinking fiber

A yarn of 650 dr/72 f was produced in the same manner as Example 1 except that the fineness of each monofilament was modified. This fiber was named "yarn A" and its performance characteristics are shown in Table 3.

(2) Production of slowly shrinking fiber

An aqueous solution of PVA having a degree of polymerization of 1,700 and a degree of saponification of 99.9 mole percent was subjected to wet spinning in a saturated aqueous solution of $Na_2SO_4$ and the filaments were drawn (drawing ratio 4.5) in air at 40° C. and in a saturated aqueous solution of $Na_2SO_4$ at 90° C., and then, in the constant length state, dried in air at 130° C.

until bone dry and further heat-treated at 170° C. Since this kind of fiber is subject to remarkable swelling and shrinkage in water, the fiber was kept under tension sufficient to maintain it at a constant length and subjected to washing with water at 30° C. to remove adhering Na₂SO₄ and to wetting treatment including oiling, followed by hot air drying, in a taut condition, at 80° C. until the water content became 40% on the fiber basis and then at 120° C. A tow composed of the thus-obtained monofilaments having a fineness of 1.5 dr was stretch-broken on a perlok system and spun on a ring spinning frame to give a spun yarn having a cotton yarn number of 10' s/1 and a number of twist of 6.8 t/in (Z). This spun yarn was named "yarn B" and its performance characteristics are shown in Table 3.

(3) Fiber substantially incapable of shrinking upon water absorption

A commercial cotton yarn 10' s/1, which was named "yarn C", was used. Its performance characteristics are shown in Table 3.

TABLE 3

| Name | Yarn A | Yarn B | Yarn C |
|---|---|---|---|
| Classification of yarn | Fiber rapidly shrinking upon water absorption (rapidly shrinking fiber) | Fiber shrinking slowly upon water absorption | Fiber substantially incapable of shrinking upon water absorption |
| Nature of yarn | Carboxy-modified PVA fiber | PVA fiber | Cotton yarn |
| Construction of yarn | Filaments 650 dr/72 f | Spun yarn 10' s/1 (cotton yarn number) | Spun yarn 10' s/1 (cotton yarn number) |
| Number of twist of yarn (direction of twist) | 0.1 t/in (Z) | 6.8 t/in (Z) | 16 t/in (Z) |
| Shrinkage upon water absorption | 65% | 45% | 2.0% |
| Rate of shrinkage upon water absorption | 4 seconds | 50 seconds | — |
| Shrinkage stress upon water absorption | 230 mg/dr | 80 mg/dr | |
| Rate of appearance of Shrinkage stress upon water absorption | 4 seconds (for the stress to reach 150 mg/dr) | 55 seconds (for the stress to reach 50 mg/dr) | |
| Shrinkage stress at 30% shrinkage due to water absorption | 50 mg/dr | 9 mg/dr | |
| Shrinkage stress retaining capacity at 30% shrinkage due to water absorption | 40 mg/dr | 9 mg/dr | |
| Shrinkage stress after water absorption | 7 mg/dr | 9 mg/dr | — |
| Shrinkage stress after water absorption at 35° C. | 0.5 mg/dr | 10 mg/dr | |
| Strength after water absorption | 0.06 g/dr | 1.1 g/dr | 1.5 g/d |
| Weight loss due to dissolution | 17.8% | 0.5% | 0% |

(4) Production of water-absorbing shrinkage yarns

The yarn obtained above in (1), (2) and (3) were used to produce twist yarns having the following constructions.

EXAMPLES 3–6

One rapidly shrinking 650 dr/72 f yarn (yarn A) and two slowly shrinking 10' s/1 yarns (yarns B) were twisted together in the S direction on a ring twisting frame with a number of twist of 5, 8, 10.5 or 14 t/in (the twist angle for the rapidly shrinking fiber being 8.1°, 12.8°, 16.9° or 22.4°, respectively) to give a folded yarn (Example 3, 4, 5 or 6, respectively).

EXAMPLE 7

A folded yarn having the same yarn construction as in Examples 3–6 was produced in the same manner as above except that the number of twist was 5 t/in (the twist angle for the rapidly shrinking fiber being 8.0°) and that the direction of twist was the as that of the spun yarn (Z direction).

COMPARATIVE EXAMPLE 4

Three slowly shrinking 10' s/1 yarns (yarns B) alone were used to produce a twist yarn on a ring twisting frame at a number of twist of 4.8 t/in (S direction).

COMPARATIVE EXAMPLE 5

Three rapidly shrinking 650 dr/72 f yarns (yarns A) alone were used to produce a twist yarn on a ring twisting frame at a number of twist of 4.6 t/in (the twist angle for the rapidly shrinking fiber being 7.6°) (S direction).

COMPARATIVE EXAMPLE 6

A plied cord composed of the rapidly shrinking fibers (yarns A) 650 dr/72 f/1×2 was twisted at a number of first twist of 14 t/in (S) and a number of final twist of 5 t/in (S) The twist angle for the rapidly shrinking fibers was 20.7°. The same direction of twist was used so that the configuration of the twist yarn could be made compact and that the strength after water absorption could be increased.

COMPARATIVE EXAMPLE 7

On rapidly shrinking 650 dr/72 f fiber (yarn A) and two 10' s/1 fibers substantially incapable of shrinking (yarns C) were twisted together in the S direction on a ring twisting frame at a number of twist of 5 t/in. The twist angle for the rapidly shrinking fiber was 7.4°.

The performance characteristics of the yarns obtained above in Example 3–7 and Comparative Examples 4–7 are shown in Table 4.

TABLE 4

| | Example 3 | Example 4 | Example 5 | Example 6 | Example 7 | Compar. Example 4 | Compar. Example 5 | Compar. Example 6 | Compar. Example 7 |
|---|---|---|---|---|---|---|---|---|---|
| Yarn | One yarn A | Same as in | Same as in | Same as in | Same as in | Three B | Three A | Two A yarns | One A yarn |

TABLE 4-continued

| | Example 3 | Example 4 | Example 5 | Example 6 | Example 7 | Compar. Example 4 | Compar. Example 5 | Compar. Example 6 | Compar. Example 7 |
|---|---|---|---|---|---|---|---|---|---|
| construction | Two yarns B | Example 3 | Example 3 | Example 3 | Example 3 | yarns | yarns | (plied yarn) | Two C yarns |
| Number of twist (t/in) (direction of twist) | 5 (S) | 8 (S) | 10.6 (S) | 14 (S) | 5 (Z) | 4.8 (S) | 4.6 (S) | 14 (S) × 5 (S) | 5 (S) |
| Twist angle for rapidly shrinking fiber(s) (°) | 8.1 | 12.8 | 16.9 | 22.4 | 8.0 | — | 7.6 | 21.0 | 7.5 |
| Twist yarn size (dr) | 1870 | 1885 | 1912 | 2023 | 1850 | 1728 | 1951 | 1445 | 1750 |
| Shrinkage upon water absorption (%) | 82 | 84 | 80 | 75 | 73 | 45 | 93 | 86 | 72 |
| Rate of shrinkage upon water absorption (seconds) | 4 | 5 | 7 | 13 | 5 | 40 | 7 | 14 | 6 |
| Shrinkage stress upon water absorption (mg/dr) | 120 | 110 | 110 | 100 | 120 | 80 | 290 | 50 | 100 |
| Rate of appearance of shrinkage stress upon water absorption (seconds) | 5 | 6 | 8 | 22 | 5 | 51 | 4 | 120 | 6 |
| Shrinkage stress after water absorption (mg/dr) | 24 | 26 | 23 | 18 | 20 | 15 | 6 | 17 | 6 |
| Shrinkage stress after water absorption at 35° C. (mg/dr) | 27 | 27 | 24 | 20 | 22 | 19 | 1 | 8 | 0.5 |
| Strength after water absorption (g/dr) | 0.90 | 0.97 | 1.01 | 0.93 | 0.92 | 1.23 | 0.08 | 0.51 | 0.89 |

The above results clearly indicate that the twist yarns made from combinations of the rapidly shrinking yarn and slowly shrinking yarn at twist angles of not greater than 18° as obtained in Examples 3, 4, 5 and 7, which are concerned with the second invention disclosed herein, meet all the requirements put forth with respect to the preferred characteristics and to be met by the water-absorbing shrinkable yarn according to the second invention. The change in the direction of twist does not result in substantial changes in the characteristics of the water-absorbing shrinkable yarn (cf. Example 7). In Example 6, the rapidly shrinking fiber was combined with the slowly shrinking fiber at an increase twist angle to give a compact yarn. In that case, the rate of shrinkage upon water absorption and the rate of appearance of shrinkage stress upon water absorption decreased to some extent, failing to meet the requirements to be preferably met in accordance with the invention. Nevertheless, yarns having such performance characteristics are still useful as water-absorbing shrinkable yarns in a variety of applications.

On the other hand, the yarn described in Comparative Example 4 was made only of the fiber capable of slowly shrinking upon water absorption and, in this case, the rate of shrinkage upon water absorption and the rate of appearance of shrinkage stress upon water absorption were markedly low In Comparative Example 5, in which the yarn was made of the rapidly shrinking fiber alone, the yarn was quite deficient in the strength after water absorption and also unsatisfactory with respect to the shrinkage stress after water absorption and to the shrinkage stress at water absorption at 35° C. In Comparative Example 6, the yarn was made of the rapidly shrinking fiber alone and had an increased strength after water absorption as a result of compact construction of the cord. In this case, too, the rate of shrinkage upon water absorption was low and the rate of appearance of shrinkage stress upon water absorption was extremely low. Furthermore, in Comparative Example 7, in which the rapidly shrinking fiber was combined with a fiber substantially incapable of shrinking upon water absorption, the shrinkage stress after water absorption and the shrinkage stress after water absorption at 35° C. were too low.

In a further trial, the yarns shown in Table 4 were used in making disposable diapers where two yarns of the same kind were used in parallel in each of the lengthwise edges of the diaper The diapers produced were tested for practical utility by applying to babies 12 months of age after birth. The results obtained are shown below in Table 5. The water-absorbing shrinkable yarns according to the invention gave good results.

TABLE 5

| Water-absorbing yarn used in the edge portions of disposable diapers | Result of utility testing of disposable diapers |
|---|---|
| Yarn of Example 3 | No abnormalities were found. |
| Yarn of Example 4 | No abnormalities were found. |
| Yarn of Comparative Example 4 | Urine escaped from both edge portions. |
| Yarn of Comparative Example 5 | Urine escaped from both edge portions. The yarns were found broken after use. |
| Yarn of Comparative | Urine escaped from both edge |

TABLE 5-continued

| Example 7 | portions. |
| --- | --- |

EXAMPLES 8–11 AND COMPARATIVE EXAMPLES 8–10

These examples and comparative examples are concerned with the third invention disclosed herein.

<Production of rapidly shrinking yarn>

(1) Production of rapidly shrinking fiber

A 500 dr/72 f yarn was produced in the same manner as Example 1 mentioned above except that the monofilament fineness was modified. This yarn showed a shrinkage percentage upon water absorption of 62%, a rate of shrinkage upon water absorption of 4 seconds, a shrinkage stress upon water absorption of 220 mg/dr, a rate of appearance of shrinkage stress upon water absorption of 4 seconds, a shrinkage stress in a 30% shrinkage state (relative to the original length) of 55 mg/dr, and a weight loss due to dissolution of 17%, and was quite satisfactory from the viewpoint of its functionality as a rapidly shrinking fiber.

(2) Fiber shrinking slowly upon water absorption

Yarn B described above in relation to Examples 3–7 was used without any modification.

(3) Production of rapidly shrinking yarn

The rapidly shrinking 500 dr/72 f yarn mentioned above in (1) and the 10′ s/1 yarn shrinking slowly upon water absorption as described above in (2) (each one yarn) were combined to produce a folded yarn at 3 t/in (Z).

<Production of water-absorbing shrinkable fiber for nonwoven fabric manufacture>

The tow produced in the course of the production process for yarn B described in Examples 3–7 was taken out from said process, then crimped, and cut to give a cut fiber having a fiber length of 51 mm. The shrinkage of this fiber in water at 20° C. amounted to 35%.

<Non-water-absorbing non-shrinking fiber for nonwoven fabric manufacture>

A commercial vinylon cut fiber 1.5 dr×51 mm was used. The shrinkage of this fiber in water at 20° C. amounted to 3%.

<Manufacture of water-absorbing shrinkable material>

The water-absorbing shrinkable 1.5 dr×51 mm fiber for nonwoven fabric manufacture as obtained in the above manner was used to make a card web in the conventional manner. The web was subjected to needle punching (200 p/cm²×both sides) to give a nonwoven fabric having a weight of 50 g/m² and a thickness of 1.2 mm. The shrinkage of the thus-obtained nonwoven fabric in the lengthwise direction in water at 20° C. was 23% and the water absorbency was 740 g/m². This nonwoven fabric was provided with three lengthwise parallel seams at 5-mm intervals at a pitch of 3 mm using the rapidly shrinking yarn produced above in (3) as the needle thread and a yarn number 80 polyester sewing thead (cotton yarn number 80′ s/3) as the bobbin thread, to give a water-absorbing shrinkable material having a width of 2 cm (Example 8). The performance characteristics of the nonwoven fabric itself used here and of the water-absorbing shrinkable material are shown in Table 6.

The water-absorbing shrinkable fiber for non woven fabric manufacture produced in the above manner (80%) and a binder fiber NBF (product of Daiwa Spinning Colo.; core-sheath fiber, 2 dr×51 mm, the core being made of polypropylene and the sheath of polyethylene) (20%) were blended and, using the blend, a nonwoven fabric and a water-absorbing shrinkable material were manufactured in the same manner as above mentioned (Example 9). The results of testing of the nonwoven fabric itself and the water-absorbing shrinking material for performance characteristics are shown in Table 6.

The water-absorbing shrinkable fiber for nonwoven fabric manufacture as obtained in the above manner (50%) and the binder fiber NBF (50%) were blended Using the blend, a nonwoven fabric and a water-absorbing shrinkable material were made in the same manner as above (Example 10). The results of testing of these for performance characteristics are shown in Table 6.

Furthermore, a nonwoven fabric and a water-absorbing shrinkable material were manufactured in the same manner as in Example 8 except that the nonwoven fabric had a weight of 80 g/m² (Example 11). The results of testing of them for performance characteristics are shown in Table 6.

On the other hand, a nonwoven fabric and a water-absorbing shrinkable material were manufactured in the same manner as in Example 8 using the same non-water-absorbing non-shrinkable fiber for nonwoven fabric manufacture as used above (ordinary vinylon fiber) (Comparative Example 8). The results of testing of them for performance characteristics are shown in Table 6.

A further nonwoven fabric and a water-absorbing shrinkable material were manufactured in the same manner as in Example 8 except that the nonwoven fabric had a weight of 20 g/m² (Comparative Example 9). The results of testing of them for performance characteristics are shown in Table 6.

Still further, a nonwoven fabric having a weight of 30 g/m² and a thickness of 0.3 mm was manufactured from a blend of 80% of the same non-water-absorbing non-shrinkable fiber as used above (ordinary vinylon fiber) and 20% of NBF by subjecting the blend to needle punching (400 p/cm²×both sides), followed by three passages through a calender roll at 140° C. The nonwoven fabric was made up into a water-absorbing shrinkable material in the same manner as in Example 8 (Comparative Example 10). The results of testing them for performance characteristics are shown in Table 6.

<Testing of disposable diapers for practical utility>

Disposable diapers were manufactured by using, as edge materials, the water-absorbing shrinkable materials of Example 8, Example 9, Comparative Example 8, Comparative Example 9 and Comparative Example 10 and tested for practical utility by applying to babies 12 months of age after birth. The results of the test are given in Table 7. The constructions of the disposable diapers manufactured are also given in Table 7.

The results given in Table 7 indicate that when the water absorbency of the nonwoven fabric constituting the water-absorbing shrinkable material is small, its function as an auxiliary water absorbent is insufficient and urine leakage may occur. When the nonwoven fabric has a weight of not greater than 30 gm², the appearance of impression caused by constriction on the thigh is somewhat reduced as compared with the use of a water-absorbing shrinkable yarn alone but no satisfactory preventive effect can be expected. It can be further understood that even when the disposable diaper has a structure such that the water absorbent and the water-absorbing shrinkable material are not in contact with each other, satisfactory shrinkage and urinary leak-preventing effect can be obtained.

TABLE 6

|  | Example 8 | Example 9 | Example 10 | Example 11 | Compar. Example 8 | Compar. Example 9 | Compar. Example 10 |
|---|---|---|---|---|---|---|---|
| [Construction of nonwoven fabric] | | | | | | | |
| Water-absorbing shrinkable vinylon fiber (%) | 100 | 80 | 50 | 100 | — | 100 | — |
| Non-water-absorbing non-shrinkable vinylon fiber (%) | — | — | — | — | 100 | — | 80 |
| Heat-meltable binder fiber NBF (%) | — | 20 | 50 | — | — | — | 20 |
| Weight (g/m$^2$) | 50 | 50 | 50 | 80 | 50 | 20 | 30 |
| Thickness (mm) | 1.2 | 1.1 | 1.0 | 1.9 | 1.2 | 0.5 | 0.3 |
| [Performance characteristics of nonwoven fabric] | | | | | | | |
| Self-shrinkage upon water absorption (%) | 23 | 21 | 15 | 22 | 2 | 22 | 3 |
| Water absorbency (g/m$^2$) | 740 | 660 | 570 | 1100 | 600 | 290 | 120 |
| [Performance characteristics of water-absorbing shrinkable material] | | | | | | | |
| Shrinkage upon water absorbance (%) | 51 | 47 | 45 | 50 | 36 | 53 | 37 |
| Rate of shrinkage upon water absorption (seconds) | 7 | 9 | 10 | 11 | 32 | 8 | 29 |
| Shrinkage stress upon water absorption (g) | 420 | 400 | 340 | 450 | 310 | 410 | 320 |
| Rate of appearance of shrinkage stress upon water absorption (seconds) | 4 | 4 | 5 | 5 | 8 | 5 | 10 |
| Shrinkage stress after water absorption (g) | 83 | 75 | 77 | 87 | 59 | 80 | 60 |
| Strength after water absorption (kg) | 2.7 | 2.4 | 2.1 | 2.8 | 2.3 | 2.0 | 2.2 |

TABLE 7

| NO. | 1 | 2 | 3 | 4 | 5 | 6 |
|---|---|---|---|---|---|---|
| [Construction of disposable diaper] | | | | | | |
| Water-absorbing shrinkable material | Example 8 | Example 9 | Compar. Example 8 | Compar. Example 9 | Compar. Example 10 | Example 9 |
| Manner of incorporation of water-absorbing shrinkable material | Rapidly shrinking yarn on back sheet side | Same as in Example 8 | Same as in Example 8 | Same as in Example 8 | Same as in Example 8 | Same as in Example 8 |
| Relative location between water absorbent and water-absorbing shrinkable material | Out of contact | Same as in Example 8 | Same as in Example 8 | Same as in Example 8 | Same as in Example 8 | Same as in Example 8 |
| Means of leading water from within water absorbent to water-absorbing shrinkable material | None | Same as in Example 8 | Same as in Example 8 | Same as in Example 8 | Same as in Example 8 | Present (cellulosic absorbent paper) |
| [Results of utility testing] | | | | | | |
| Urinary leak from edge | None | None | Found | None | Found | None |
| Impression caused by constriction | None | None | None | Remarkable | Little remarkable | None |
| Stuffiness (rash) | None | None | None | None | None | Found |

What is claimed is:

1. A water-absorbing shrinkable mix-twisted or mix-spun yarn which comprises a first fiber capable of rapidly shrinking upon absorption of water and a second fiber capable of shrinking more slowly than the former fiber upon absorption of water, said first fiber being characterized in that the maximum shrinkage percentage in water at 20° C. is not less than 30%, with the time required for the shrinkage percentage to reach 30% being not longer than 10 seconds, that the shrinkage stress in water at 20° C. as measured in the original length state is not less than 150 mg/dr, with the time required for the shrinkage stress of 150 mg/dr to appear being not longer than 10 seconds, that the shrinkage stress in water at 20° C. as measured in the state of 30% shrinkage relative to the original length is not less than 30 mg/dr and that the weight loss due to dissolution upon dispersion in water at 20° C. is not more than 45%, and wherein said first fiber is made of a carboxyl group-containing modified polyvinyl alcohol, and said second fiber is made of unmodified polyvinyl alcohol.

2. The water-absorbing shrinkable yarn of claim 1, wherein said first fiber is characterized in that the shrinkage stress in water at 20° C. as measured in the original length state is not less than 30 mg/dr, with the time required for the shrinkage stress of 30 mg/dr to appear being not longer than 10 seconds and that the shrinkage stress and the strength as measured in the wet state after 16 hours of immersion in water at 20° C. in the state of 30% shrinkage relative to the original length are not less than 10 mg/dr and not less than 300 mg/dr, respectively.

3. The water-absorbing shrinkable yarn of claim 1, wherein the twist angle of the fiber capable of rapidly shrinking upon absorption of water is not more than 18°.

4. The water-absorbing shrinkable yarn of claim 1, wherein said second fiber capable of shrinking more slowly upon absorption of water is characterized in that the maximum shrinkage percentage in water at 20° C. is not less than 30%, with the time required for the shrinkage percentage to reach 30% being 10 seconds to 5 minutes, that the shrinkage stress in water at 20° C. as measured in the original length state is not less than 50 mg/dr, with the time required for the shrinkage stress of 50 mg/dr to appear being 10 seconds to 5 minutes and that the shrinkage stress and the strength as measured in the wet state after 16 hours of immersion in water at 20° C. in the state of 30% shrinkage relative to the original length are not less than 5 mg/dr and not less than 500 mg/dr, respectively.

* * * * *